United States Patent [19]

Machida et al.

[11] Patent Number: 5,663,391
[45] Date of Patent: Sep. 2, 1997

[54] MANUFACTURING PROCESS FOR PRODUCING A β COPPER DIKETONE COMPLEX

[75] Inventors: Hideaki Machida; Hiroshi Kokubun, both of Hachioji, Japan

[73] Assignee: Tri-Chemical Laboratory, Inc., Yamanashi Pref., Japan

[21] Appl. No.: 611,654

[22] Filed: Mar. 6, 1996

[30] Foreign Application Priority Data

Mar. 7, 1995 [JP] Japan ................... 7-046821

[51] Int. Cl.$^6$ ................ C07F 1/08; C07F 19/00
[52] U.S. Cl. ............. 556/12; 556/114; 556/117; 427/587; 117/104
[58] Field of Search ............. 556/117, 12, 114; 117/104; 427/587

[56] References Cited

U.S. PATENT DOCUMENTS

| | | | |
|---|---|---|---|
| 4,385,005 | 5/1983 | Doyle | 260/464 |
| 4,425,281 | 1/1984 | Doyle | 260/430 |
| 5,085,731 | 2/1992 | Norman et al. | 156/646 |
| 5,098,516 | 3/1992 | Normal et al. | 156/666 |
| 5,187,300 | 2/1993 | Norman | 556/12 |
| 5,322,712 | 6/1994 | Norman et al. | 427/250 |

OTHER PUBLICATIONS

Thomas H. Baum and Carl E. Larson, "Chemical Vapor Deposited Copper from Alkyne Stabilized Copper (1) Hexafluoroacetylacetonate Complexes", *J. Electrochem, So vol. 140, No. 1*, Jan. 1993© The Electrochemical Society, Inc.

*Primary Examiner*—Porfirio Nazario-Gonzalez

[57] ABSTRACT

A process for producing a β copper diketone complex which consists of the steps: (a) mixing and reacting $Cu_2O$, 1,1,1,5,5,5-Hexafluoro-2, 4-pentanedione, and an additional cuprous L, an electronic donator; and (b) dehydrating the crude material, which is performed at the same time and/or right after the reaction in step (a).

7 Claims, 1 Drawing Sheet

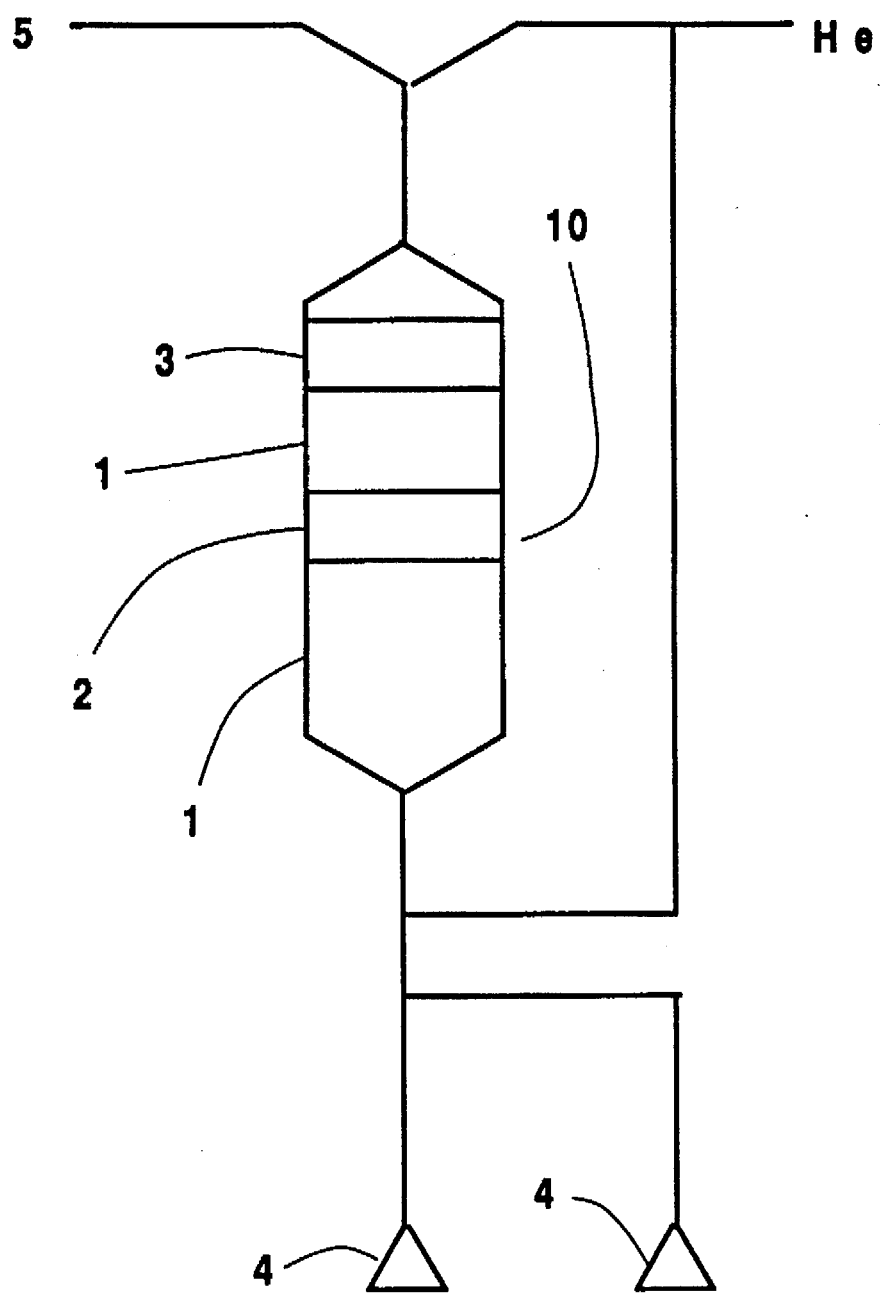

MANUFACTURING PROCESS FOR PRODUCING A β COPPER DIKETONE COMPLEX

TECHNICAL FIELD OF THE INVENTION

The invention relates to a process for manufacturing a high-purity β copper diketone complex for chemical vapor deposition (CVD) which is used for forming thin membranes containing copper.

BACKGROUND OF THE INVENTION

Recently, chemical vapor deposition has been used in the manufacturing procedures for thin copper membranes. For example, CVD is used for the manufacturing of thin membranes for superconductors, copper wiring for various ICs, and compound semiconductors (called chalcopyrite) such as $Cu_x In_y$ (Al, CA) $S_n$ (Se).

The material for this CVD is, for example the β Copper diketone complex shown in Exhibit 1.

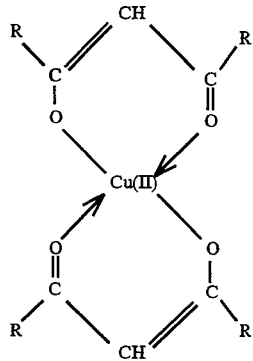

Exhibit 1

[R is a methyl radical, t is a butyl radical or a trifluoromethyl radical.]

This compound is not suitable for CVD, where a sublimation transportation is used. This compound is solid; thus, it is not suitable for a mass transportation. It is also not suitable for industrial production due to its high disintegration temperature and the slow speed at which it forms thin copper membranes.

To solve this problem, a β copper diketone complex consisting HfaCu(I).L is developed as shown in Exhibit 2.

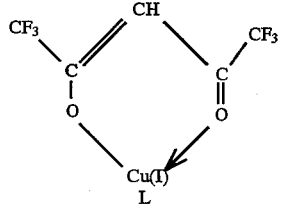

Exhibit 2

[L is an additional cuprous, an electronic donator.]

The compound shown in Exhibit 2 is suitable for CVD because its fusing point is below 100° C., L is liquid when it is TMVS, and the compound's steam pressure is higher than the one for the compound shown in Exhibit 1.

The following method 1 is known as composite procedures:

(1) $Cu_2O+2Hfa(H)+2L \rightarrow 2HfaCu.L+H_2O$ [Hfa (H)=1,1,1,5,5,5-Hexaflouoro-2, 4-pentanedione]

Currently, this method is not used for industrial production because HfaCu.L disintegrates in a short time.

(2) $CuX+HfaM+L \rightarrow HfaCu.L+MX$ [X is a halogen atom, M is alkali metal such as Li, Na, K.]

This method 2 does not have the problem of the method (1), the HfaCu.L disintegrates in a short time. However, it has a contamination problem with halogen atoms and alkali metals. A distillate purification is performed to remove these impurities; however, the yield is reduced significantly due to the instability of HfaCu.L.

Also, the separation of HfaCu.L and the crude materials, such as HfaNa, are difficult due to the materials' steam pressure. This makes it difficult to acquire high-purity HfaCu.L. Moreover, the materials, such as CuX and HfaM are expensive; thus, method (2) costs 10 times more than method (1).

An object of the subject invention is to provide a high-purity copper complex (a β copper diketone complex) such as HfaCu(I).L, shown in Exhibit 2, at a low cost.

This invention regards the manufacturing procedures of a β copper diketone complex which consist of: the first process, mixing and reacting $Cu_2O$, 1, 1, 1, 5, 5, 5-Hexafluoro-2, 4-pentanedione and an additional cuprous L, an electronic donator; and the second process, dehydrating the crude material such as by using a dehydrating agent, which is performed at the same time and/or right after the reaction in the first process.

This invention also regards the manufacturing procedures of a β copper diketone complex which consist of: the third process, the purification of the crude material via a column chromatogram (for example, a column chromatogram filled with silica gel and/or alumina).

BRIEF DESCRIPTION OF THE DRAWING

The single drawing is a diagram of a purification device 10 (a column) which 1 is silica gel, 2 is alumina, 3 is dehydrating agent, 4 is a pan and 5 is an input line for the crude material.

The dehydrating agent can be any agent that does not give a negative impact on the reaction, such as copper sulfate, sodium sulfate, magnesium sulfate, and/or molecular sieves.

The additional cuprous L, an electronic donator, for the HfaCu.L (a β copper diketone complex) is selected from the following [I], [II], [III], or [IV].

[I] $R_1 \equiv R_2$

[$R_1$ and $R_2$ are hydrocarbon radicals with 1–8 carbon atoms or organic radicals with 1–8 carbon atoms consisting Si.]

[II] $R_3$ ($R_4$) ($R_5$)

[$R_3$, $R_4$ and $R_5$ are hydrogen atoms or hydrocarbon radicals with 1–6 argon atoms.]

[III] Ring hydrocarbon with 5–18 carbon atoms, which may have more than two double bonds.

[It is also allowable to have side chain (s).]

[IV] $R_6(R_7)$ $(R_8)Si—(CH_2)_n—C(R_9)=CR_{10}(R_{11})$

[$R_6$, $R_7$, $R_8$, $R_9$, $R_{10}$, $R_{11}$ are hydrogen atoms, hydrocarbon radicals with 1–6 carbon atoms, or organic radicals with 1–6 carbon atoms constituting Si ",$_n$,"=0, 1, Or 2.]

The filling for the column chromatogram (such as silica gel and/or alumina), used in the third process, should be dehydrated. Also, the filling should be dehydrated (preferably, dehydrated and oxygen removed) either at low degree of vacuum (less than 30 mmHg, preferably less than 20 mmHg, more preferably less than 10 mmHg) and/or at high temperature (higher than 100° C.).

After the dehydration, the filling should be treated under the ambient pressure using a solvent. The solvent should be dehydrated, and oxygen/inert gases are removed. Also, the column should consist of layers of dehydrating agents.

The third process should be performed without touching moisture and/or oxygen. The process includes filtering, purification, and removal of impurities.

The purification in the column can be performed without a solvent. This is because HfaCu.TMVS is liquid at room temperature, and the purification does not require an organic solvent.

Following is a detailed explanation of this invention: This invention is based on the compound method (1): $Cu_2O+2Hfa(H)+2L \rightarrow 2HfaCu.L+H_2O$.

Since method (2) does not solve the cost problem, method (1) is further studies. The problem with method (1) is that the HfaCu.L disintegrates in a short time. If this problem could be solved, the method (1) is suitable for CVD. Method (1) does not have the cost problem, contaminating problem with halogen atoms and alkali metals, reduced yield problem due to removal of impurities, and the difficulty of acquiring high-purity HfaCu.L.

The problem that HfaCu.L disintegrates in a short time in method (1) was further studied. The result showed that the problem was caused by by-product water. That is, HfaCu.L is sensitive to water, and the by-product water causes a disintegration of HfaCu.L.

This problem can be solved by removing the by-product water. A dehydrating agent is added to the material before, at the same time, and/or right after the reaction. High-purity HfaCu.L is acquired by a purification via a column filled with dehydrated filling.

Following is the detailed explanation of this invention using test results.

Test 1: Add 81 g (1.45 mol) of 2-butyne ($CH_3C \equiv CCH_3$ (L)) to the reacting container containing 325 g (2.27 mol) of cuprous oxide ($Cu_2O$) and 2 liters of dichloromethane ($CH_2Cl_2$), and stir for 30 minutes. Then, add 300 g (1.44 mol) of 1,1,1,5,5,5-Hexafluoro-2, 4-pentanedione (Hfa(H)), and make the reaction of $Cu_2O+2Hfa(H)+2L \rightarrow 2HfaCu.L+H_2O$.

The color of the solution has been changed to yellow-green. At this moment magnesium sulfuric anhydride is added.

40 minutes later, non-reacted cuprous oxide and magnesium sulfate are filtered, and dichloromethane is concentrated. 375 g of yellow-green solid body (HfaCu.L (L:$CH3C \equiv CCH_3$) is acquired at a yield of 79%.

Test 2: The crude materials acquired is purified in the column filled with silica gel. The silica gel is dehydrated for an hour at 100° C. and under 0.1 mmHg, and is treated under the ambient pressure. Dichloromethane, just distillated from calcium hydride, is used as the solvent.

The yellow-green solid is separated to green impurities and yellow HfaCu.L. The HfaCu.L is stable for a long time.

The results of element analyses are as follows:

Theoretical amount: C: 33.29% H: 2.17%

Measured amount: C: 33.20% H: 2.04%

The amounts of halogen and metals: $Cl^-$, $Br^-$, and $Li^+$ are less than the possible amount to detect, $Na^+$ is 44 ppb, and $K^+$ is 5 ppb.

Test 3: 172 g (1.2 mol) of cuprous oxide ($Cu_2O$) and 40 g (0.25 mol) of dehydrated copper sulfate ($CuSO_4$) are suspended in chloroform that is dehydrated and deaerated. 166 g (0.8 mol) of TMVS is added, and stirred for 30 minutes. Then, 360 g (0.8 mol) of Hfa(H) is added to cause a reaction.

One hour later, the solid body is filtered, and the filtrate is concentrated. Crude HfaCu.TMVS is acquired at a yield of 80%.

Test 4–6: The same results are acquired when using $Na_2SO_4$, $MgSO_4$, or molecular sieves instead of $CuSO_4$ as a dehydrating agent in Test 3.

Test 7–9: The same results are acquired when using 2-butyne, 1,5-COD, $(CH_3)_3SiC \equiv CSi(CH_3)_3$ instead of TMVS in Test 3.

Test 10–11: The same results are acquired when using tetrahydrofuran or cyclohexane instead of chloroform as a solvent in Test 3.

Test 12: The HfaCu(I).TMVS acquired in Test 3, is purified in the column filled with silica gel and alumina (purification device 10). In purification device 10, 1 is the silica gel that is dehydrated with the same procedures in Test 2, 2 is the alumina that is dehydrated with the same procedures in Test 2, 3 is the dehydrating agent, 4 is the pan, 5 is the entry for the crude material. A solvent is not needed for HfaCu(I) .TMVS since it is liquid.

The yellow-green liquid is separated to green impurities and yellow HfaCu(I).TMVS. This HfaCu(I).TMVS is stable for a long time.

The results of element analyses are as follows:

Theoretical amount: C: 33.85% H: 3.69%

Measured amount: C: 32.43% H: 3.30%

The results of proton chemical shift δ checked by NMR is as follows:

δ- 0.42(S,9H); δ0.41(m,1H); δ4.25(m, 2H); δ6.15(S,1H)

The amounts of halogen and metals: $Cl^-$, $Br^-$, and $Li^+$ are less than the possible amount to detect, $Na^+$ is 44 ppb, and $K^+$ is 5 ppb.

Test 13 and 14: The HfaCu(I).L, acquired in Test 8 and 9, are purified in the column 10 Used in Test 12. The mixture of normal hexane and methylene chloride (2:8) is used as the solvent. The yield is more than 90%.

The result of element analyses are as follows:

[HfaCu.1, 5-COD]

Theoretical amount: C: 41.22% H: 3.46%

Measured amount: C: 41.11% H: 3.55%

[HfaCu.$(CH_3)_3SiC \equiv CSiCH_3)_3$]

Theoretical amount: C: 35.41% H: 4.34%

Measured amount: C: 35.01% H: 4.20%

Both materials are stable for a long time.

Comparison 1: A test using the same procedures for Test 1, except magnesium sulfuric anhydride was not added, was conducted; and a greenish solid body was acquired at a yield of 70%. Copper was attached on the inner wall of the container and HfaCu.L disintegrated in the concentration process.

Comparison 2: The amount of halogen and metals in HfaCu.L (after the purification): $Cl^-$ is 2 μg/ml, $Br^-$ is 270 μg/ml, $Na^+$ is 49 ppb, and $K^+$ is 5 ppb. This HfaCu.L contains a lot of impurities, especially halogen impurities. $Na^+$ was 72 ppm before the purification.

Conclusion: High purity HfaCu(I).L, a β copper diketone complex, is provided at a low cost.

What is claimed:

1. A process for producing a β copper diketone complex which consist of the steps: (a) mixing and reacting $Cu_2O$, 1,1,1,5,5,5-Hexafluoro-2, 4-pentanedione and an additional cuprous L, an electronic donator; and (b) dehydrating the crude material of step (a).

2. The process of claim 1 wherein in step (b) a dehydrating agent is used for dehydrating the crude material.

3. The process of claim 1 wherein the additional cuprous L, an electronic donator, is selected from the group consisting of (I), (II), (III) and (IV) wherein (1) $R_1 \equiv R_2$

[$R_1$ and $R_2$ are hydrocarbon radicals with 1–8 carbon atoms or organic radicals with 1–8 carbon atoms consisting Si.];

(2) $R_3$ ($R_4$) ($R_5$)

[$R_3$, $R_4$ and $R_5$ are hydrogen atoms or hydrocarbon radicals with 1–6 argon atoms.];

(3) Ring hydrocarbon with 5–18 carbon atoms, which may have more than two double bonds.

(4) $R_6(R_7)(R_8)Si-(CH_2)_n-C(R_9)=CR_{10}(R_{11})$ ($R_6$, $R_7$, $R_8$, $R_9$, $R_{10}$, $R_{11}$ are hydrogen atoms, hydrocarbon radicals with 1–6 carbon atoms, or organic radicals with 1–6 carbon atoms constituting Si. "$n$" =0, 1, or 2.).

4. The process of claim 1 wherein after step (b) the following step is added: (c) purifying of the crude material in a column chromatogram filled with at least one filling agent selected from the group consisting of silica gel and alumina.

5. The process of claim 2 wherein the dehydrating agent is selected from one of the groups consisting of copper sulfate, sodium sulfate, magnesium sulfate and molecular sieves.

6. The process of claim 4 wherein the filling agent for the column is dehydrated.

7. The process of claim 4 wherein the column contains two or more layers of the dehydrating agents.

* * * * *